US012775105B2

(12) United States Patent
Li et al.

(10) Patent No.: US 12,775,105 B2
(45) Date of Patent: Oct. 27, 2026

(54) DETECTING APPARATUS COMPRISING A FLAT PANEL DETECTOR HAVING A PLURALITY OF BIAS SIGNAL LINES AND A PLURALITY OF SHORT-CIRCUITING BARS

(71) Applicants: Beijing BOE Sensor Technology Co., Ltd., Beijing (CN); BOE Technology Group Co., Ltd., Beijing (CN)

(72) Inventors: Jinyu Li, Beijing (CN); Xuecheng Hou, Beijing (CN); Zhenyu Wang, Beijing (CN)

(73) Assignees: Beijing BOE Sensor Technology Co., Ltd., Beijing (CN); Beijing BOE Technology Development Co., Ltd., Beijing (CN)

( * ) Notice: Subject to any disclaimer, the term of this patent is extended or adjusted under 35 U.S.C. 154(b) by 202 days.

(21) Appl. No.: 18/578,354

(22) PCT Filed: Aug. 3, 2022

(86) PCT No.: PCT/CN2022/109893
§ 371 (c)(1),
(2) Date: Jan. 11, 2024

(87) PCT Pub. No.: WO2023/011508
PCT Pub. Date: Feb. 9, 2023

(65) Prior Publication Data

US 2024/0337764 A1 Oct. 10, 2024

(30) Foreign Application Priority Data

Aug. 5, 2021 (CN) ......................... 202110896697.5

(51) Int. Cl.
*A61B 6/42* (2024.01)
*G01N 23/04* (2018.01)
*G01T 1/20* (2006.01)

(52) U.S. Cl.
CPC ........ *G01T 1/20182* (2020.05); *A61B 6/4233* (2013.01)

(58) Field of Classification Search
CPC ....... A61B 6/42; A61B 6/4208; A61B 6/4233; A61B 6/4258; A61B 6/4266;
(Continued)

(56) References Cited

U.S. PATENT DOCUMENTS 6,399,950 B1 * 6/2002 Kimura ................... G01T 1/241 250/370.11
6,849,853 B2 * 2/2005 Ikeda .................. H10F 39/1892 250/370.09

(Continued)

FOREIGN PATENT DOCUMENTS

CN 101064786 A 10/2007
CN 101930077 A 12/2010

(Continued)

*Primary Examiner* — Allen C. Ho
(74) *Attorney, Agent, or Firm* — HOUTTEMAN LAW LLC

(57) ABSTRACT

A flat panel detector and a detecting apparatus. The flat panel detector includes a base substrate, and scanning lines, data lines, signal lines and detecting units in an array on the base substrate; each detecting unit includes a switch sub-circuit and a photosensitive device; control terminals of switch sub-circuits in detecting units in a same row are connected with a same scanning line; first terminals of switch sub-circuits in detecting units in a same column are connected with a same data line; in each detecting unit, a second terminal of the switch sub-circuit is connected with a first terminal of the photosensitive device; second terminals of photosensitive devices of the detecting units in the same column are connected with a same bias signal line, the bias signal lines are divided into groups, the bias signal lines in different groups are mutually insulated and connected with different driving chips.

15 Claims, 8 Drawing Sheets

(58) Field of Classification Search
CPC ...... A61B 6/4283; G01N 23/04; G01N 23/10; G01N 23/16; G01N 23/18; G01T 1/16; G01T 1/17; G01T 1/20; G01T 1/2006; G01T 1/2018; G01T 1/20182; G01T 1/20184; G01T 1/20185; G01T 1/20186; G01T 1/20187; G01T 1/20188; G01T 1/24; G01T 1/241; G01T 1/243; G01T 1/244; G01T 1/247; G01T 1/248; G01T 1/249; G01T 1/29; G01T 1/2914; G01T 1/2928
USPC ..................................... 250/370.09; 378/98.8
See application file for complete search history.

(56) References Cited

U.S. PATENT DOCUMENTS

| | | | | |
|---|---|---|---|---|
| 7,767,974 | B2 * | 8/2010 | Jung | H10D 86/00 250/370.09 |
| 7,985,954 | B2 * | 7/2011 | Jung | G01T 1/20184 250/370.09 |
| 8,106,364 | B2 * | 1/2012 | Jung | G01T 1/20184 250/370.11 |
| 8,384,041 | B2 * | 2/2013 | Tredwell | H10F 39/1898 250/370.11 |
| 8,476,596 | B2 * | 7/2013 | Shin | H10F 39/016 250/370.08 |
| 8,748,835 | B2 * | 6/2014 | Lim | G01T 1/20184 250/370.09 |
| 8,785,994 | B2 * | 7/2014 | Kim | G01T 1/20183 257/E31.115 |
| 8,803,061 | B2 * | 8/2014 | Stamm | H04N 25/626 348/308 |
| 8,803,210 | B2 * | 8/2014 | Jung | H10F 39/1898 257/292 |
| 8,916,830 | B2 * | 12/2014 | Lim | G01T 1/2928 250/370.11 |
| 9,269,740 | B2 * | 2/2016 | Kim | H10F 39/189 |
| 9,287,315 | B2 * | 3/2016 | Kim | H10K 39/36 |
| 9,589,855 | B2 * | 3/2017 | Iwata | H01L 22/14 |
| 9,716,125 | B2 * | 7/2017 | La Casce | A61B 6/542 |
| 10,185,042 | B2 * | 1/2019 | Yoon | G01T 1/247 |
| 10,353,082 | B2 * | 7/2019 | Tomiyasu | G01T 1/20 |
| 10,381,396 | B2 * | 8/2019 | Tomiyasu | G01T 1/20 |
| 10,386,503 | B2 * | 8/2019 | Jung | G01T 1/2018 |
| 10,431,610 | B2 * | 10/2019 | Cho | H10D 86/0231 |
| 10,802,163 | B2 * | 10/2020 | Yi | G01T 1/247 |
| 11,169,283 | B2 * | 11/2021 | Jeon | G01T 1/2018 |
| 11,296,139 | B2 * | 4/2022 | Jeon | G01T 1/2018 |
| 11,309,451 | B2 * | 4/2022 | Hou | H04N 25/30 |
| 11,309,457 | B2 * | 4/2022 | Jeon | H10H 20/815 |
| 11,404,469 | B2 * | 8/2022 | Zhang | H10F 39/016 |
| 11,604,291 | B2 * | 3/2023 | Li | G01T 1/241 |
| 12,270,957 | B2 * | 4/2025 | Moriwaki | G01T 1/2018 |
| 12,461,254 | B2 * | 11/2025 | Zhang | G01T 1/20182 |
| 2010/0051819 | A1 | 3/2010 | Jung et al. | |
| 2011/0180889 | A1 | 7/2011 | Jung et al. | |

FOREIGN PATENT DOCUMENTS

| | | | |
|---|---|---|---|
| CN | 104604216 | A | 5/2015 |
| CN | 105592797 | A | 5/2016 |
| CN | 107134467 | A | 9/2017 |
| CN | 108318907 | A | 7/2018 |
| JP | 2009219538 | A | 10/2009 |
| JP | 2016003966 | A | 1/2016 |

* cited by examiner

DETECTING APPARATUS COMPRISING A FLAT PANEL DETECTOR HAVING A PLURALITY OF BIAS SIGNAL LINES AND A PLURALITY OF SHORT-CIRCUITING BARS

TECHNICAL FIELD

The present disclosure relates to the field of flat panel detection technology, and particularly relates to a flat panel detector and a detecting apparatus.

BACKGROUND

With the continuous development of flat panel detection technology in recent years, manufacturers and researchers have brought the flat panel X-ray detector (FPXD) from laboratory to clinical use, and due to the advantages of high sensitivity, wide dynamic range, low distortion of digital images, and the like, the flat panel X-ray detector is widely applied to the fields of medical radiation imaging, industrial flaw detection, security inspection, and the like. The flat panel X-ray detector includes an array substrate, where the array substrate includes an X-ray conversion layer and detecting units, the X-ray conversion layer may be made of a scintillator material, and each detecting unit includes a thin film transistor and a photodiode. When the array substrate is irradiated by X rays, the X rays are converted into visible light by the X-ray conversion layer, then the visible light is converted into electric signals by the photodiodes in the detecting units, and the electric signals are processed to obtain desired image information.

The inventor finds that the conventional flat panel X-ray detector has a problem of high noise, and therefore, providing a flat panel X-ray detector with low noise is an urgent problem to be solved.

SUMMARY

The present disclosure is directed to solve at least one of the problems of the prior art and to provide a flat panel detector.

The present disclosure provides a flat panel detector, which includes a base substrate, and a plurality of scanning lines, a plurality of data lines, a plurality of bias signal lines and a plurality of detecting units arranged in an array, which are disposed on the base substrate; each of the plurality of detecting units includes a switch sub-circuit and a photosensitive device; control terminals of switch sub-circuits in detecting units located in a same row are connected with a same scanning line; first terminals of switch sub-circuits in detecting units located in a same column are connected with a same data line; in each detecting unit, a second terminal of the switch sub-circuit is connected with a first terminal of the photosensitive device; second terminals of photosensitive devices of the detecting units located in the same column are connected with a same bias signal line, where the plurality of bias signal lines are divided into a plurality of signal line groups, the bias signal lines in different signal line groups are insulated from each other and are connected with different driving chips.

In some implementations, each of the bias signal lines includes a first end and a second end that are oppositely disposed in a column direction, first ends of the bias signal lines in a same signal line group are connected with each other by a first short-circuiting bar, and second ends of the bias signal lines are connected with each other by a second short-circuiting bar; each first short-circuiting bar is connected with one of the driving chips, and/or each second short-circuiting bar is connected with one of the driving chips.

In some implementations, each of the bias signal lines includes a first end and a second end that are oppositely disposed in a column direction, first ends of the bias signal lines of one of two adjacent signal line groups are connected with each other by a first short-circuiting bar, and second ends of the bias signal lines of the other of the two adjacent signal line groups are connected with each other by a second short-circuiting bar, and each first short-circuiting bar is connected with one of the driving chips, and each second short-circuiting bar is connected with one of the driving chips.

In some implementations, each of the plurality of bias signal lines includes a first signal sub-line and a second signal sub-line arranged side by side in a column direction, and the photosensitive devices connected to the first signal sub-line and the second signal sub-line are different;

for any signal line group, ends of first signal sub-lines away from second signal sub-lines are connected with each other by a first short-circuiting bar, and ends of the second signal sub-lines away from the first signal sub-lines are connected with each other by a second short-circuiting bar; each first short-circuiting bar is connected with one of the driving chips, and each second short-circuiting bar is connected with one of the driving chips.

In some implementations, the switch sub-circuit includes a thin film transistor, a first electrode of the thin film transistor is connected with a data line, a second electrode of the thin film transistor is connected with a photosensitive device, and a control electrode of the thin film transistor is connected with a scanning line; the thin film transistor is configured to write an electric signal generated by the photosensitive device into the data line under control of a control signal of the scanning line.

In some implementations, the thin film transistor includes an amorphous silicon thin film transistor or a metal oxide thin film transistor.

In some implementations, a photoelectric conversion layer is provided on a side of the detecting unit away from the base substrate, and the photoelectric conversion layer is configured to convert an external electric signal into an optical signal.

In some implementations, the photosensitive device includes a photodiode; a first electrode of the photodiode is connected with the thin film transistor, and a second electrode of the photodiode is connected with the bias signal line; the photodiode is configured to convert the optical signal received into an electric signal under an action of a bias voltage of the bias signal line, and input the electric signal to the second electrode of the thin film transistor.

In some implementations, the photodiode includes a PIN type photodiode.

On the other hand, the present disclosure further provides a detecting apparatus, which includes the above flat panel detector.

DETAIL DESCRIPTION OF EMBODIMENTS

In order to enable those skilled in the art better understand the technical solutions of the present disclosure, the following detailed description is given with reference to the accompanying drawings and specific implementations.

Unless defined otherwise, technical or scientific terms used herein shall have the ordinary meaning as understood by one of ordinary skill in the art to which the present disclosure belongs. The terms "first", "second", and the like in this disclosure are not intended to indicate any order, quantity, or importance, but rather are used to distinguish one element from another. Also, the term "a", "an", "the", or the like does not denote a limitation of quantity, but rather denotes the presence of at least one. The term "comprising/including", "comprises/includes", or the like means that the element or item preceding the term includes the element or item listed after the term and its equivalent, but does not exclude other elements or items. The term "connected/coupled", "connecting/coupling", or the like is not restricted to physical or mechanical connections, but may include electrical connections, whether direct or indirect. The terms "upper", "lower", "left", "right", and the like are used only to indicate relative positional relationships, and when the absolute position of the object being described is changed, the relative positional relationships may also be changed accordingly.

The transistors used in the embodiments of the present disclosure may be thin film transistors or field effect transistors or other devices with the same characteristics, and since a source and a drain of each transistor used are symmetrical, there is no difference in functions of the source and the drain. In addition, the transistors can be divided into N-type transistors and P-type transistors according to the characteristics of the transistors, and in the following embodiments, the N-type transistors are adopted for explanation, when the N-type transistors are used, a first electrode is a drain electrode of the N-type transistor, a second electrode is a source electrode of the N-type transistor, and when the high level is input to a gate electrode, the source and drain electrodes are conducted, which is opposite for the P-type transistor. It is contemplated that implementation with P-type transistors will be readily apparent to one skilled in the art without creative effort, and thus, are within the scope of embodiments of the present disclosure.

Figure 1:
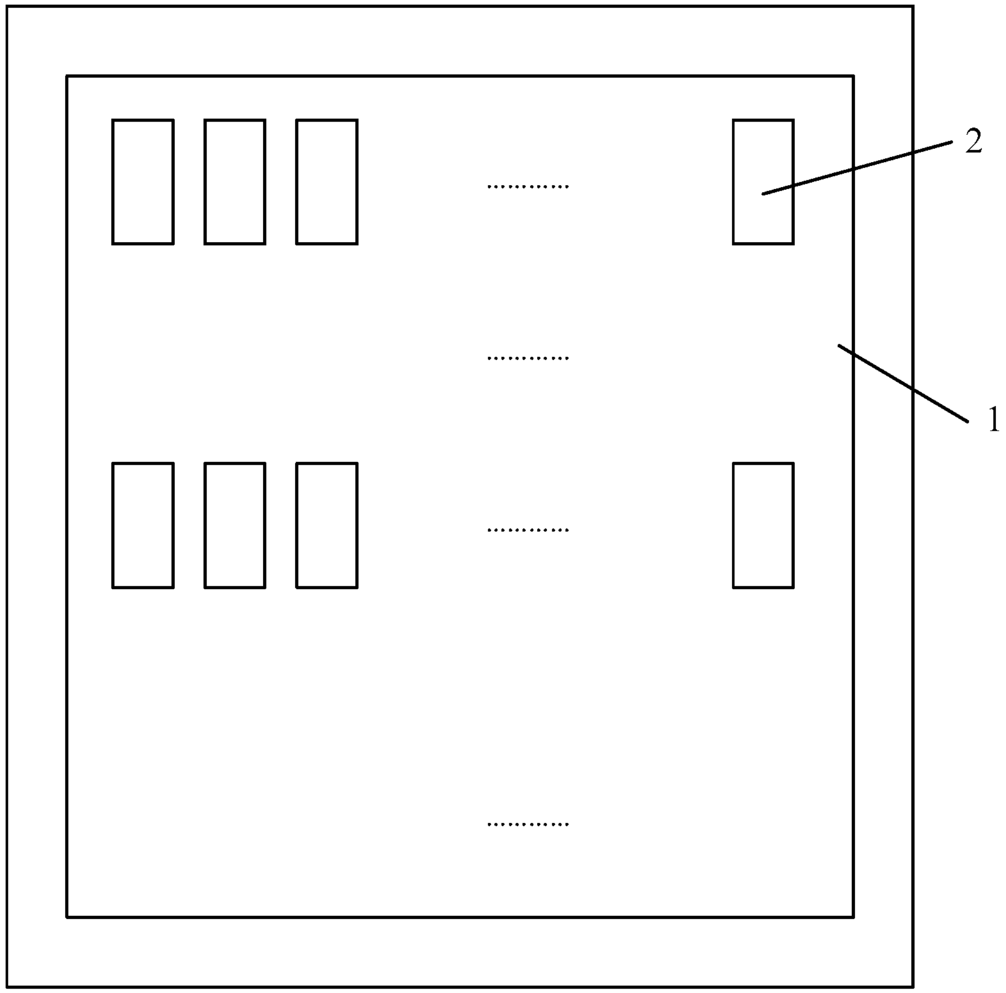
FIG. 1 is a schematic diagram of a base substrate and a detecting unit of an exemplary flat panel detector.

FIGS. 1 to 5 show an exemplary flat panel detector, and FIG. 1 shows a base substrate 1 of the flat panel detector, where the base substrate 1 includes a plurality of detecting units 2 arranged in an array along a first direction and a second direction; the first direction intersects the second direction, one of the first direction or the second direction may be a row direction, and the other of the first direction or the second direction may be a column direction. In embodiments of the present disclosure, the first direction is taken as the row direction, and the second direction is taken as the column direction for description.

Figure 2:
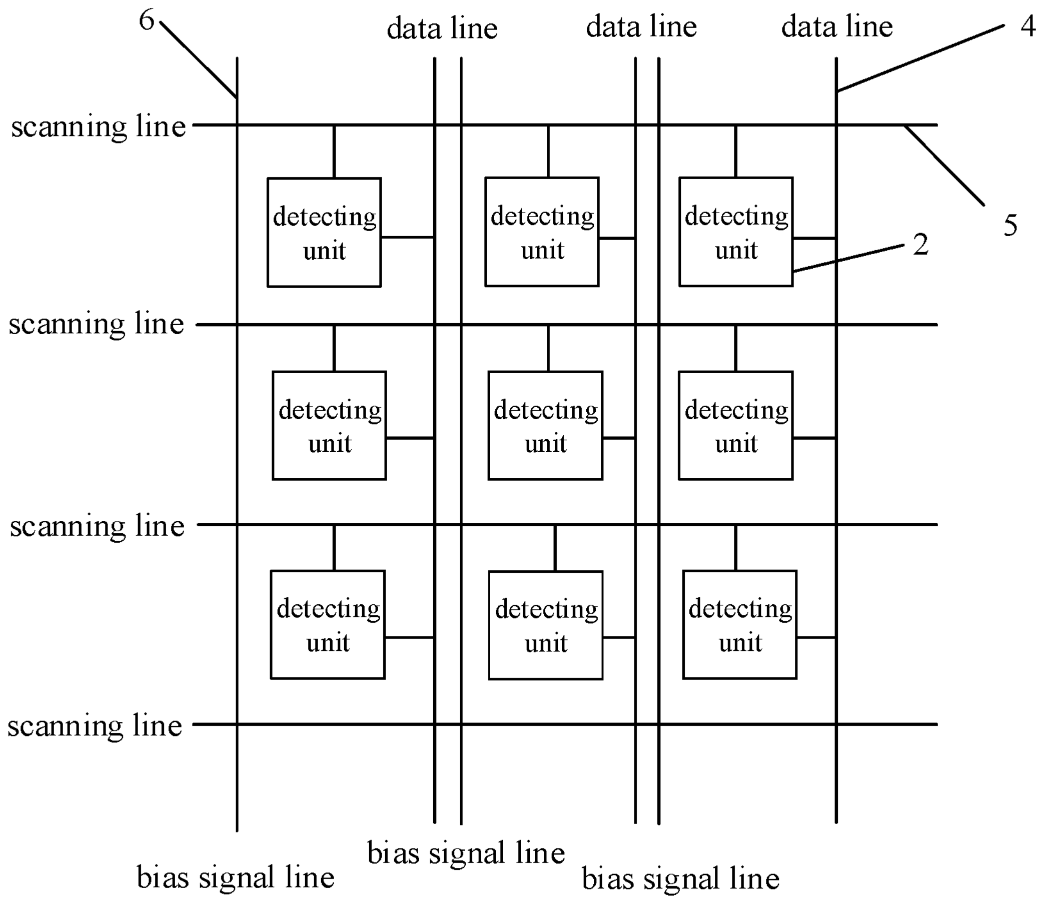
FIG. 2 is a schematic diagram of a detecting unit of an exemplary flat panel detector.

As shown in FIG. 2, the base substrate 1 further includes a plurality of data lines 4 and a plurality of scanning lines 5, where the detecting units 2 in a same row are connected to a same scanning line 5, and the detecting units 2 in a same column are connected to a same data line 4. Each scanning line 5 is configured to output a control signal, and the control signal control the detecting units 2 in the same row to operate and output corresponding electric signals to the data lines 4.

Figure 3:
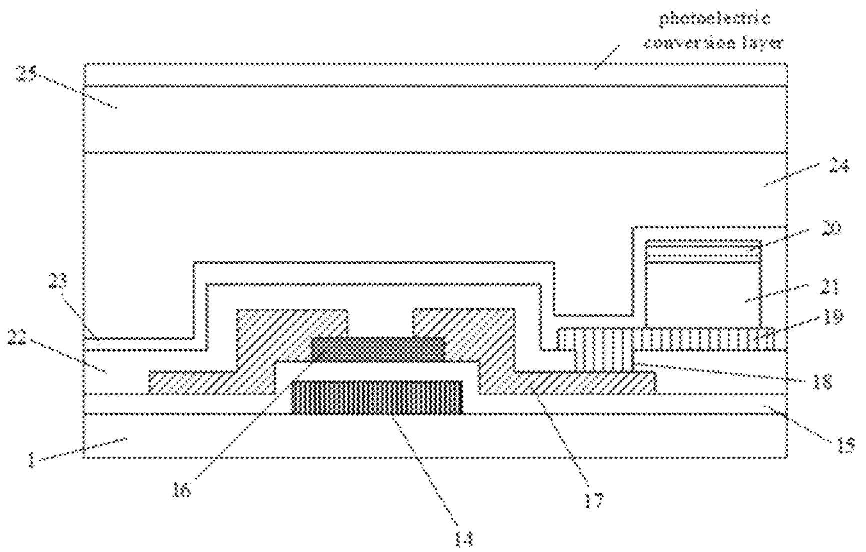
FIG. 3 is a cross-sectional view of a detecting unit of an exemplary flat panel detector.

As shown in FIG. 3, FIG. 3 is a schematic cross-sectional diagram of a structure of the detecting unit 2, and a main structure of the flat panel detector includes a base substrate 1, a photodiode 13 and a thin film transistor 11 disposed on the base substrate 1, a planarization layer 24 covering the photodiode 13 and the thin film transistor 11, and a scintillation layer 25 disposed on the planarization layer 24. Generally, the photodiode 13 includes an anode, a cathode, and a semiconductor layer 21, and the thin film transistor 11 includes a gate 14, a gate insulating layer 15, an active layer 16, a source, and a drain.

The gate 14 of the thin film transistor 11 is disposed on the base substrate 1, the gate insulating layer 15 is disposed on a side of the base substrate 1 and the gate 14 of the thin film transistor 11 away from the base substrate 1, the active layer 16 is disposed on a side of the gate insulating layer 15 away from the base substrate 1, the source and the drain are formed on a first metal layer 17, the first metal layer 17 being disposed on a side of the gate insulating layer 15 and the active layer 16 away from the base substrate 1. A first insulating layer 22 is disposed on a side of the first metal layer 17 away from the base substrate 1, and a first conductive layer 19 is disposed on a side of the first insulating layer 22 away from the base substrate 1, and penetrates through the first insulating layer 22 to be connected with the drain of the thin film transistor 11. The first conductive layer 19 includes the cathode of the photodiode 13. The semiconductor layer 21 of the photodiode 13 is disposed on a side of the first conductive layer 19 away from the base substrate 1, the semiconductor layer 21 includes an N-type semiconductor layer 21, an intrinsic semiconductor layer 21, and a P-type semiconductor layer 21, and the N-type semiconductor layer 21 of the photodiode 13 is connected to the first conductive layer 19. A second conductive layer 20 is disposed on a side of the cathode of the photodiode 13 away from the base substrate 1, the second conductive layer 20 including the anode of the photodiode 13. A second insulating layer 23 is disposed on a side of the first conductive layer 19, the first insulating layer 22 and the second conductive layer 20 away from the base substrate 1, and the planarization layer 24 and the scintillation layer 25 are sequentially disposed on a side of the second insulating layer 23 away from the base substrate 1.

In this example, the gate 14, the gate insulating layer 15, the active layer 16, and the first metal layer 17 constitute the structure of the above-described thin film transistor 11; the active layer 16 is used to form a conductive channel of the thin film transistor 11, and the first metal layer 17 is used to constitute the source and the drain of the thin film transistor 11. The first insulating layer 22 is used to protect the active layer 16 and the source and the drain of the thin film transistor 11. The first conductive layer 19 is used to form the cathode of the photodiode 13, and the first conductive layer 19 is used to electrically connect the drain of the thin film transistor 11 with the cathode of the photodiode 13. The second conductive layer 20 includes the anode of the photodiode 13, and the second conductive layer 20 is used to output an electric signal of the photodiode 13. The second insulating layer 23 is used to protect the thin film transistor 11 and the photodiode 13, and the planarization layer 24 is used to planarize the structures of the thin film transistor 11 and the photodiode 13 and to facilitate the arrangement of the scintillator layer 25. The scintillation layer 25 is used to convert X-rays projected onto a surface of the flat panel detector into visible light.

In this example, a method for manufacturing the thin film transistor 11 and the photodiode 13 in the detecting unit 2 may include the following steps S11 to S17.

At step S11, the gate 14, the gate insulating layer 15, and the active layer 16 of the thin film transistor 11 and the first metal layer 17 are sequentially formed on the base substrate through a patterning process.

In the present embodiment, the base substrate may be made of a transparent material such as glass, and may be pre-cleaned. Specifically, first, a gate metal film layer is formed on the base substrate by a sputtering method, a thermal evaporation method, a plasma enhanced chemical vapor deposition (PECVD) method, a low pressure chemical vapor deposition (LPCVD) method, an atmospheric pressure chemical vapor deposition (APCVD) method, or an electron cyclotron resonance chemical vapor deposition (ECR-CVD) method. Then, a pattern of the gate 14 is formed by using a halftone mask (HTM) or a graytone mask (GTM) through a patterning process (which includes film formation, exposure, development, wet etching or dry etching). The gate 14 may be made of a metal or a metal alloy, such as molybdenum, molybdenum-niobium alloy, aluminum, aluminum-neodymium alloy, titanium, copper, or other conductive materials.

Next, the gate insulating layer 15 is formed on the gate 14 by using the plasma enhanced chemical vapor deposition method, the low pressure chemical vapor deposition method, the atmospheric pressure chemical vapor deposition method, the electron cyclotron resonance chemical vapor deposition method, or the sputtering method. Then, an amorphous silicon film is deposited on the gate insulating layer 15 by the plasma enhanced chemical vapor deposition method, the low pressure chemical vapor deposition method, or the like, and the amorphous silicon film is crystallized and subjected to a patterning process to form a pattern of the active layer 16.

Finally, the first metal layer 17 is formed on the gate and the gate insulating layer by the plasma enhanced chemical vapor deposition method, the low pressure chemical vapor deposition method, the atmospheric pressure chemical vapor deposition method, the electron cyclotron resonance chemical vapor deposition method, or the sputtering method, and the first metal layer 17 is subjected to a single patterning process to form a pattern including the source and the drain of the thin film transistor 11.

At step S12, the first insulating layer 22 is formed through a patterning process, and a first via hole 18 is formed to penetrate the first insulating layer 22 at a position of the first insulating layer 22 corresponding to the drain.

Specifically, in this step, a passivation film layer may be deposited by the plasma enhanced chemical vapor deposition method, the low pressure chemical vapor deposition method, the atmospheric pressure chemical vapor deposition method, or the electron cyclotron resonance chemical vapor deposition method, and the passivation film layer is subjected to a patterning process including masking, dry etching and the like to form the first via hole 18. The first insulating layer 22 is an inorganic insulating layer formed of silicon nitride (SiNx), an inorganic insulating layer formed of silicon oxide ($SiO_2$), or a composite film layer in which at least one inorganic insulating layer made of SiNx and at least one inorganic insulating layer made of $SiO_2$ are stacked.

At step S13, a pattern including the cathode of the photodiode 13 is formed through a patterning process, and the pattern is connected to the drain of the thin film transistor 11 through the first via hole 18.

Similar to the formation process of the source and the drain of the thin film transistor 11, in this step, the first conductive layer 19 may be deposited on the first insulating layer 22 by the plasma enhanced chemical vapor deposition method, the low pressure chemical vapor deposition method, the atmospheric pressure chemical vapor deposition method, the electron cyclotron resonance chemical vapor deposition method, or the sputtering method, and the first conductive layer 19 may be subjected to a patterning process, including masking, wet etching and the like, to form a pattern of the cathode of the photodiode 13.

The first conductive layer 19 may be made of a conductive material such as a metal or a metal alloy, for example, molybdenum, molybdenum-niobium alloy, aluminum, aluminum-neodymium alloy, titanium or copper.

At step S14, a semiconductor material layer is deposited on the first conductive layer 19, and a patterning process is performed on the semiconductor material layer to form a pattern including the semiconductor layer 21 of the photodiode 13.

In the present embodiment, the base substrate of the flat panel detector includes a photodiode region, and the semiconductor layer 21 is located at a position, corresponding to the photodiode region, on the base substrate. The semiconductor material layer may specifically include an N-type semiconductor material layer, an I-type semiconductor material layer, and a P-type semiconductor material layer. The semiconductor material layer is deposited on an etching block material layer by the plasma enhanced chemical vapor deposition method or the low pressure chemical vapor deposition method.

A portion of the semiconductor material layer outside the photodiode region is removed by a dry etching process such as a plasma etching (PE), a reactive ion etching (RIE), an enhanced capacitive coupled plasma etching (ECCP), and an inductively coupled plasma etching (ICP) to form the semiconductor layer 21.

At step S15, a pattern including the anode of the photodiode 13 is formed through a patterning process, the anode of the photodiode 13 being disposed on a side of the semiconductor layer 21 away from the base substrate 1, and being connected with the semiconductor layer 21.

In this step, the second conductive layer 20 may be deposited on the semiconductor layer 21 by the plasma enhanced chemical vapor deposition method, the low pressure chemical vapor deposition method, the atmospheric pressure chemical vapor deposition method, the electron cyclotron resonance chemical vapor deposition method, or the sputtering method, and the second conductive layer 20 is subjected to a patterning process such as masking and wet etching to form a pattern of the anode of the photodiode 13. A material of the second conductive layer 20 may be a conductive material such as a metal or a metal alloy, for example, molybdenum, molybdenum-niobium alloy, aluminum, aluminum-neodymium alloy, titanium or copper.

At step S16, the second insulating layer 23 is formed on the first insulating layer 22 and the photodiode 13, where the forming process and material of the second insulating layer 23 may be similar to those of the first insulating layer 22, and therefore are not described herein again.

At step S17, the planarization layer 24 is formed on the second insulating layer 23.

A material of the planarization layer 24 includes resin, and a thickness thereof is relatively large so as to play a planarizing function on the base substrate of the flat panel detector. Specifically, similar to the formation of the first insulating layer 22, in this step, the planarization layer 24 may be deposited by the plasma enhanced chemical vapor deposition method, the low pressure chemical vapor deposition method, the atmospheric pressure chemical vapor deposition method, or the electron cyclotron resonance chemical vapor deposition method.

The material of the planarization layer 24 may include an organic insulating material, for example, a resin material such as polyimide, epoxy, acrylic, polyester, photoresist, polyacrylate, polyamide, siloxane. As another example, the organic insulating material includes an elastic material, such as urethane, and thermoplastic polyurethane (TPU).

So far, the manufacturing of the thin film transistor 11 and the photodiode 13 on the base substrate of the flat panel detector is completed.

Figure 4:
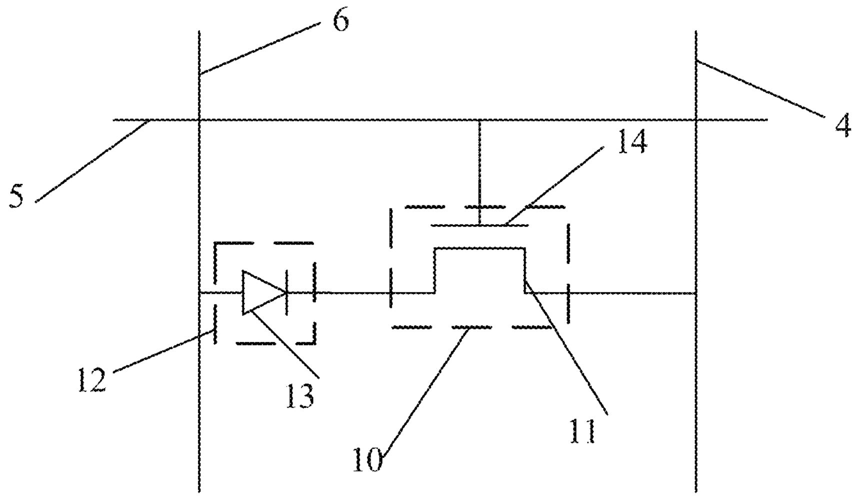
FIG. 4 is an equivalent circuit diagram of a detecting unit of an exemplary flat panel detector.

FIG. 4 is a structure of the detecting unit 2, and the detecting unit 2 includes a switch sub-circuit 10 and a photosensitive device 12, where a control terminal of the switch sub-circuit 10 is connected to the scanning line 5, and control terminals of switch sub-circuits 10 in a same row are connected to a same scanning line 5; a first terminal of the switch sub-circuit 10 is connected to the data line 4, and first terminals of switch sub-circuits 10 in a same column are connected to a same data line 4; a second terminal of the switch sub-circuit 10 is connected to a first terminal of the photosensitive device 12; a second terminal of the photosensitive device 12 is connected to a bias signal line 6, and second terminals of photosensitive devices 12 in a same column is connected to a same bias signal line 6. The scanning line 5 turns on the switch sub-circuit 10 by a control signal, the bias signal line 6 provides a bias signal for the above-mentioned photosensitive device 12, the photosensitive device 12 converts an optical signal received into an electric signal, and outputs an operation signal to the data line 4 through the switch sub-circuit 10. Specifically, the switch sub-circuit 10 may be a thin film transistor 11, and the photosensitive device 12 may be the photodiode 13. The first terminal of the switch sub-circuit 10 is a source of the thin film transistor 11, the second terminal of the switch sub-circuit 10 is a drain of the thin film transistor 11, and the control terminal of the switch sub-circuit 10 is a gate 14 of the thin film transistor 11; the first terminal of the photosensitive device 12 is the cathode of the photodiode 13, and the second terminal of the photosensitive device 12 is the anode of the photodiode 13.

Figure 5:
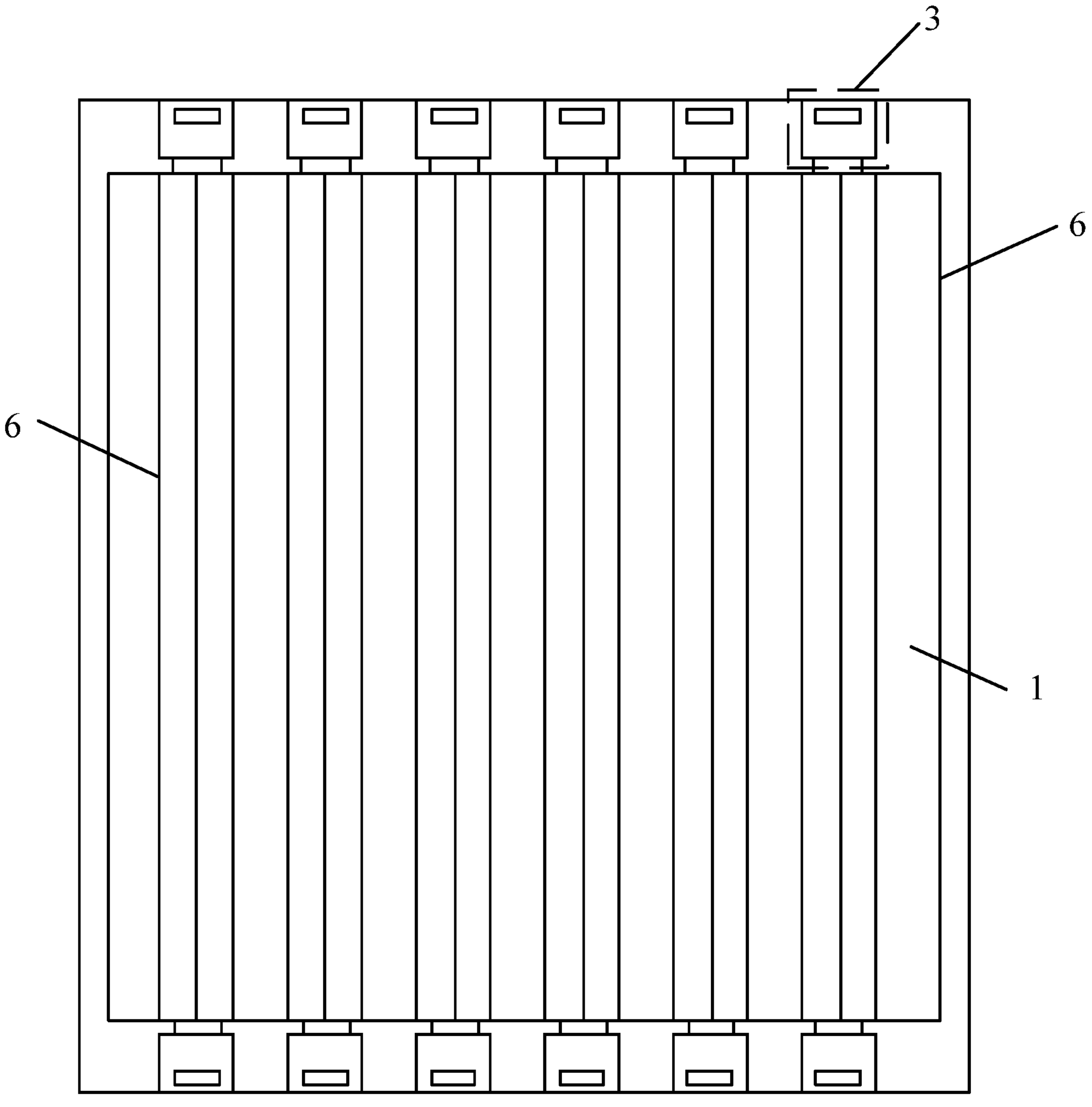
FIG. 5 is a schematic diagram of exemplary bias signal lines disposed on a base substrate.

As shown in FIG. 5, the base substrate 1 further includes a plurality of bias signal lines 6, detecting units 2 located in a same column are connected to a same bias signal line 6, and a ring-shaped bias signal line 6 is disposed in an edge area of the plurality of detecting units, and the ring-shaped bias signal line 6 is electrically connected with (short-circuited with) the bias signal lines 6 arranged along the second direction. That is, all the bias signal lines 6 on the base substrate 1 are short-circuited. The ring-shaped bias signal line 6 is connected with different driving chips 3, and the driving chips 3 are arranged at both ends of the bias signal lines 6 arranged in the second direction. The bias signal line 6 is configured to output a bias signal to provide a bias voltage for the detecting unit 2.

A working principle of the flat panel detector is as follows: X-rays are modulated by a human body on their way, the modulated X-rays are converted into visible light by the scintillation layer 25, the photodiode 13 absorbs the visible light and converts it into charge carriers, which are stored in a storage capacitor or a self capacitor of the photodiode 13 to form a charge image, the plurality of rows of thin film transistors 11 are sequentially turned on by a scan driving circuit, and charge images of a same row of thin film transistors are simultaneously readout and output to the data lines 4. The charge images output from all the thin film transistors 11 are processed to generate a desired detection image.

In practical applications, the inventors found that, since the bias signal lines 6 disposed in the second direction on the exemplary base substrate 1 are short-circuited with the ring-shaped bias signal line 6 disposed in the edge area of the detecting units 2, and therefore the bias signal lines 6 on the base substrate 1 are connected as a whole (that is, connected with each other). In a case where one of the driving chips 3 connected to the bias signal lines 6 is interfered and thus there is a deviation in the bias signal output from the driving chip, all the detecting units 2 on the base substrate 1 are affected since the bias signal lines 6 are connected as whole, thereby generating a large noise. Meanwhile, since the bias signal lines 6 are connected as a whole, the driving chip 3 susceptible to interference and the bias signal lines 6 cannot be specifically adjusted.

In view of the problems in the prior art, the inventor improves the prior art.

In a first aspect, as shown in FIGS. 1 to 8, an embodiment of the present disclosure provides a flat panel detector, which includes a base substrate 1, and a plurality of scanning lines 5, a plurality of data lines 4, a plurality of bias signal lines 6 and a plurality of detecting units 2 arranged in an array, which are disposed on the base substrate 1, where each detecting unit 2 includes a switch sub-circuit 10 and a photosensitive device 12, control terminals of switch sub-circuits 10 in detecting units 2 located in a same row are connected to a same scanning line 5, first terminals of switch sub-circuits 10 in detecting units 2 located in a same column are connected to a same data line 4, and in each detecting unit 2, a second terminal of the switch sub-circuit 10 is connected to a first terminal of the photosensitive device 12; second terminals of photosensive devices 12 of the detecting units 2 located in the same column are connected to a same bias signal line 6. The plurality of bias signal lines 6 are divided into a plurality of signal line groups, and the bias signal lines 6 in different signal line groups are insulated from each other and connected to different driving chips 3.

In the present embodiment, since the plurality of bias signal lines are divided into the plurality of signal line groups, the bias signal lines in different signal line groups are insulated from each other, and different signal line groups connect with different driving chips 3, in a case a certain driving chip 3 is interfered and there is a deviation in the bias signal output from the certain driving chip 3, only the bias signal of the signal line group connected with the certain driving chip 3 is affected, only the detecting units 2 connected with this signal line group are affected, and the noise is reduced. Furthermore, since each independent driving chip 3 is connected with the signal line group which is insulated from any other signal line group, the driving load of the driving chip 3 is relatively small, and when the bias signal of the signal line group is affected by external interference, the bias signal of the signal line group can be quickly restored to be normal, and the noise is reduced. Moreover, specific optimization adjustment can be performed on certain driving chips 3 or signal line groups, so that a grayscale image, obtained after an output operation signal is processed, is more uniform.

Figure 6:
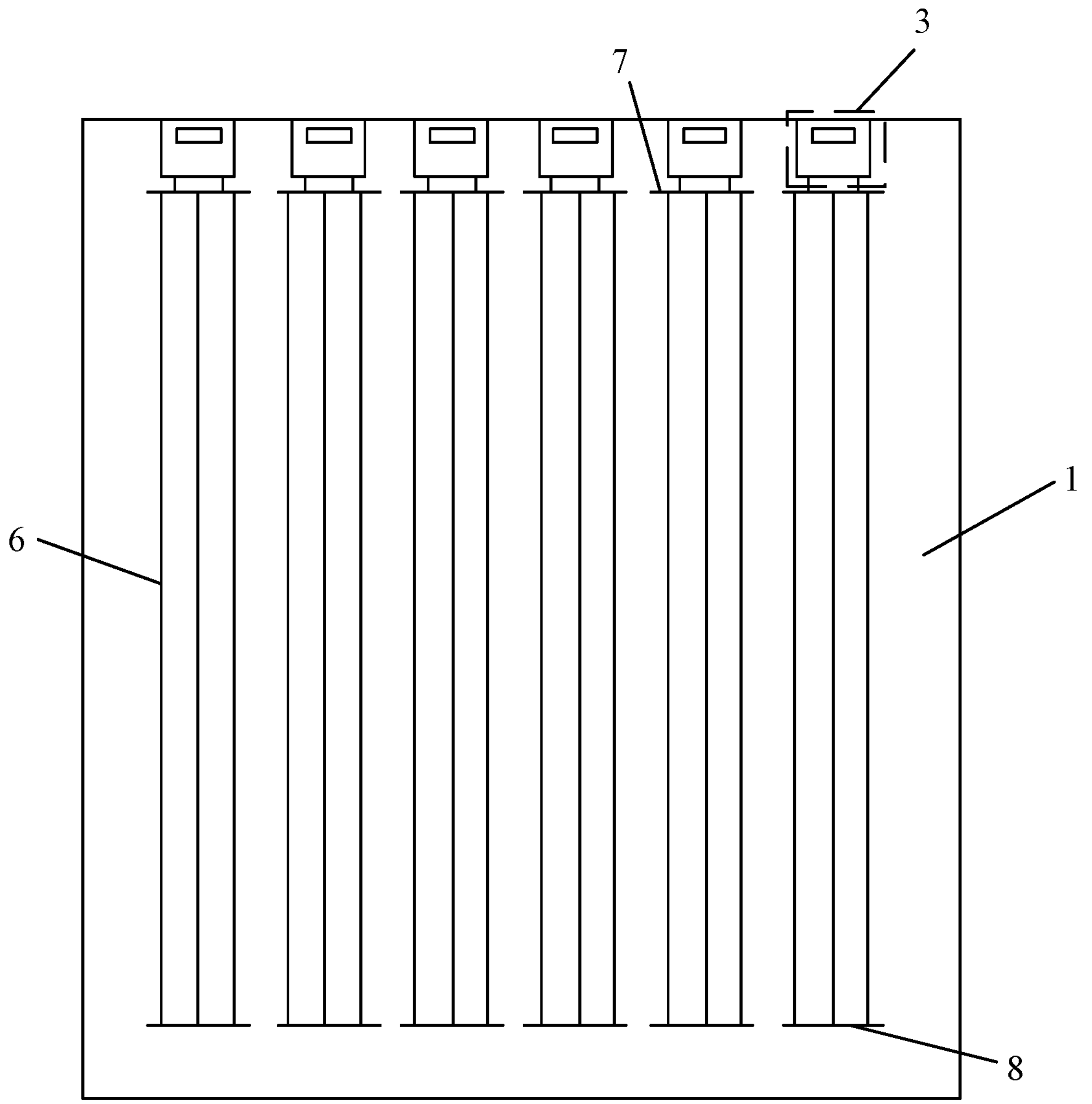
FIG. 6 is a schematic diagram of bias signal lines disposed on a base substrate according to an embodiment of the present disclosure.
Figure 7:
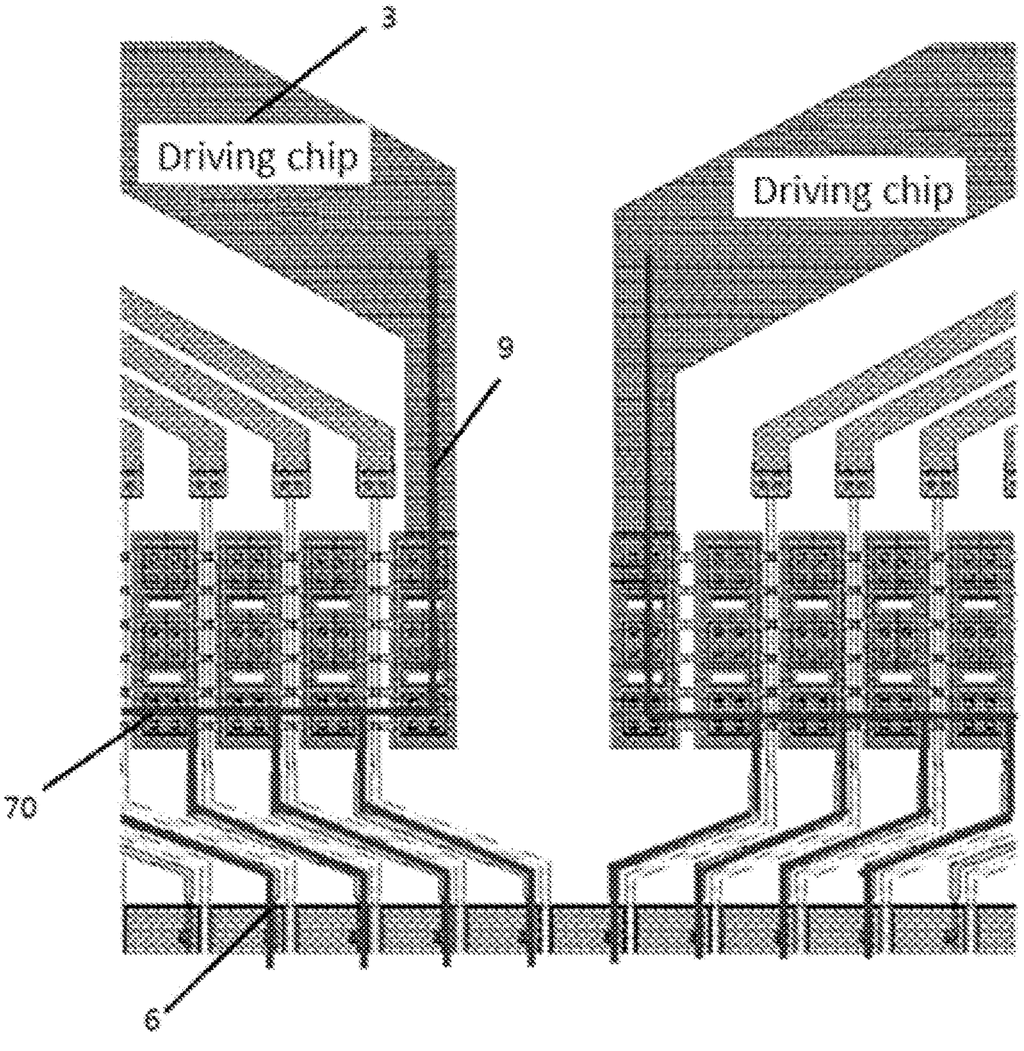
FIG. 7 is a partial layout of a flat panel detector according to an embodiment of the present disclosure.

As shown in FIG. 6, in some implementations, the bias signal lines 6 of the flat panel detector in the present embodiment each include a first end and a second end oppositely arranged in the second direction, first ends of the bias signal lines 6 in a same signal line group are connected with each other by a first short-circuiting bar 7, and second ends of the bias signal lines 6 in the same signal line group are connected with each other by a second short-circuiting bar 8. Each first short-circuiting bar 7 is connected to one driving chip 3, and/or each second short-circuiting bar 8 is connected to one driving chip 3. Furthermore, FIG. 7 is a partial layout of the flat panel detector according to the embodiment of the present disclosure, and as can be seen from FIG. 7, the bias signal lines 6 in the same signal group extend from a detection area to a peripheral area, and end portions (the first ends or the second ends) of the bias signal lines 6 are connected together by the short-circuiting bar 70, and then are bound and connected with the driving chip 3 by a signal lead-out line 9. For example, the signal lead-out line is connected with a first connection pad in the peripheral area, and the first connection pad is connected with a second connection pad on the driving chip 3, so that the bias signal lines 6 in a same signal group are connected with a same driving chip 3. In addition, the driving chips 3 connected to the bias signal lines 6 in different signal groups are different.

In this case, as shown in FIG. 6, the driving chips 3 are all arranged at a same end of the signal line groups along the first direction, and the driving chips 3 are respectively connected to different ones of the signal line groups, and the signal line groups are insulated from each other. Since the above-described bias signal lines 6 are divided into signal line groups insulated from each other and each signal line group is individually connected to the driving chip 3, and the driving chips 3 are provided only at a same end of the bias signal lines. The driving chips 3 are arranged at only a same end of the bias signal lines 6, so that the manufacturing cost of the flat panel detector is reduced. Meanwhile, the driving chips 3 are only arranged at a same end of the bias signal lines 6, so that the probability that the output signal of the driving chip 3 is influenced due to an external interference is reduced.

Figure 8:
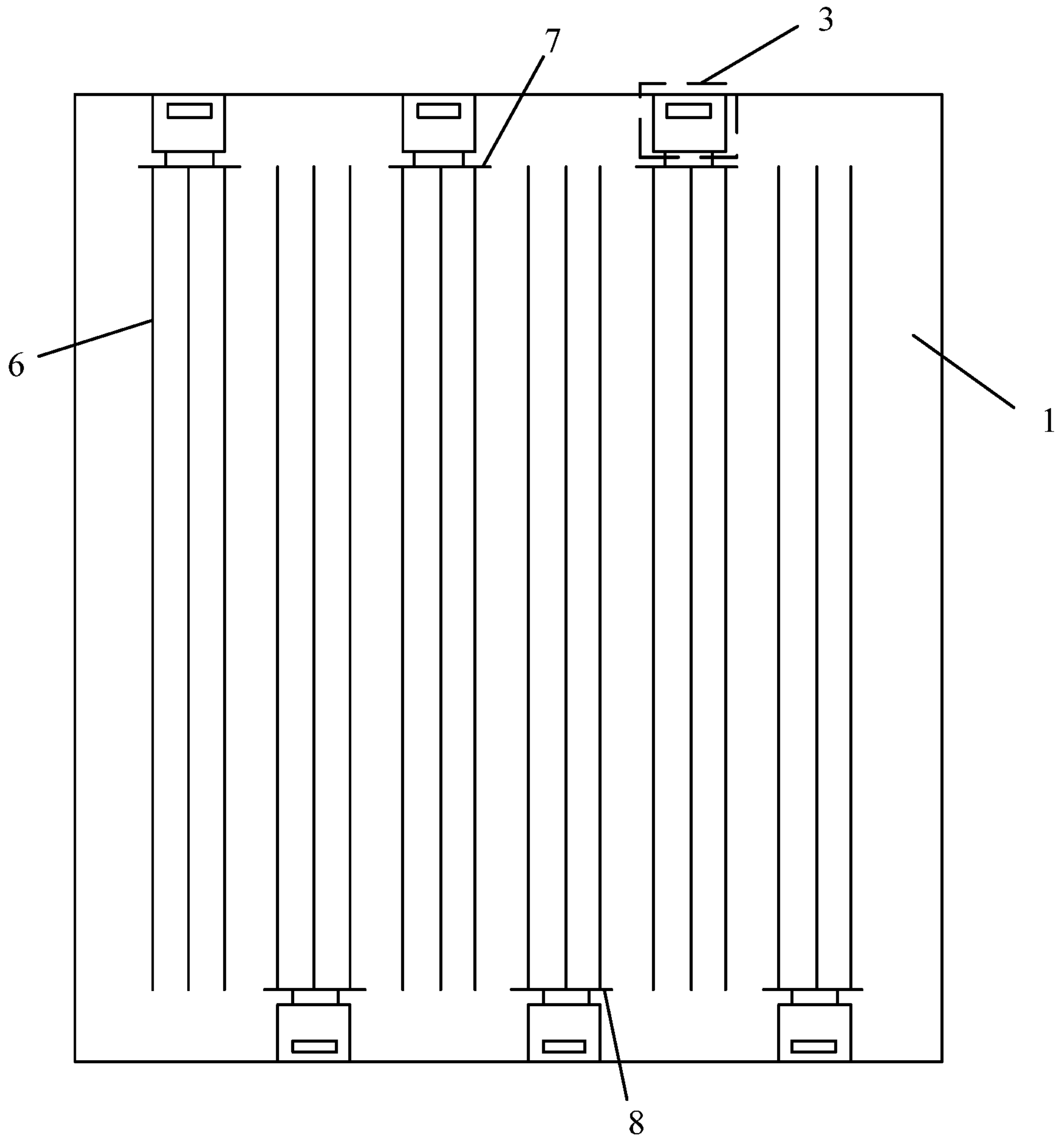
FIG. 8 is a schematic diagram of bias signal lines disposed on a base substrate according to an embodiment of the present disclosure.

As shown in FIG. 8, in some implementations, the flat panel detector in the embodiment may alternatively have the following structure: each bias signal line 6 includes a first end and a second end arranged oppositely in the second direction, first ends of the bias signal lines 6 in one of two adjacent signal line groups are connected with each other by a first short-circuiting bar 7, second ends of the bias signal lines 6 in the other one of the two adjacent signal line groups are connected with each other by a second short-circuiting bar 8, where the first short-circuiting bar 7 is connected with one driving chip 3, and the second short-circuiting bar 8 is connected with another driving chip 3.

In this case, as shown in FIG. 8, since the first ends of the respective bias signal lines 6 in one of the two adjacent signal line groups are connected with each other by the first short-circuiting bar 7 and the second ends of the respective bias signal lines 6 in the other of the two adjacent signal line groups are connected with each other by the second short-circuiting bar 8, the first short-circuiting bar 7 and the second short-circuiting bar 8 are connected to the driving chips 3, respectively. Therefore, the driving chips 3 connected to the two adjacent signal line groups are respectively located on two opposite sides of the base substrate 1 along the second direction. Since the driving chips 3 are disposed on two opposite sides of the base substrate 1 along the second direction, on one side of the base substrate 1 along the second direction, the driving chips 3 are disposed such that the driving chips 3 are respectively connected to the signal line groups spaced apart by a signal line group therebetween, so that on one side of the base substrate 1 along the second direction, every two adjacent driving chips 3 have an interval therebetween greater than a size of the driving chip 3 which is beneficial to specific optimization adjustment of certain driving chips 3 or signal line groups, and thus the grayscale image, obtained after an output operation signal is processed, is more uniform.

Figure 9:
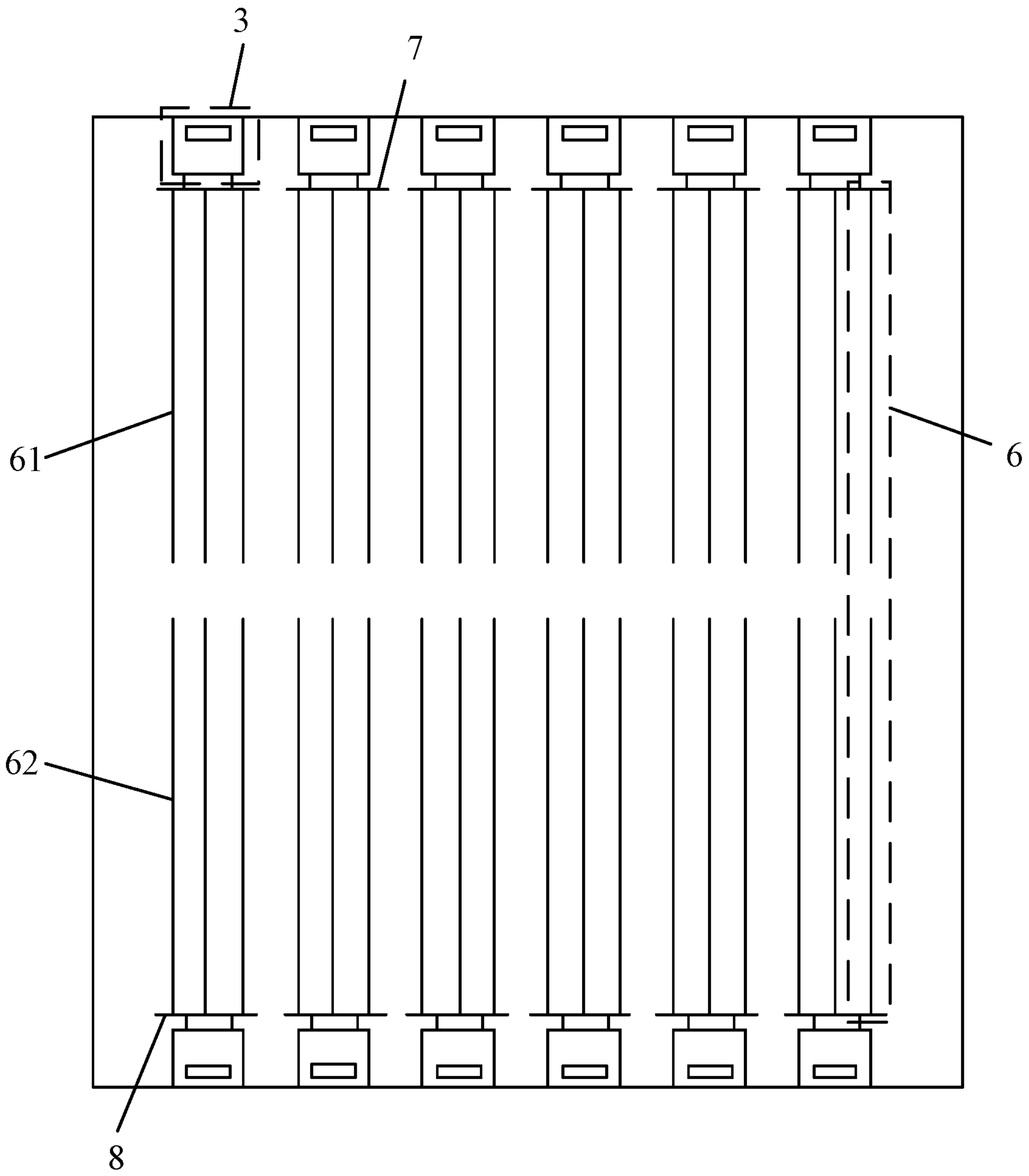
FIG. 9 is a schematic diagram of bias signal lines disposed on a base substrate of an embodiment of the present disclosure.

As shown in FIG. 9, in some implementations, the bias signal lines 6 of the flat panel detector in this embodiment may alternatively be configured as follows: each of the plurality of bias signal lines 6 includes a first signal sub-line 61 and a second signal sub-line 62 disposed side by side in the second direction, and the photosensitive devices 12 to which the first signal sub-line 61 and the second signal sub-line 62 are connected are different; for any signal line group, ends of first signal sub-lines 61 away from second signal sub-lines 62 are electrically connected with each other through a first short-circuiting bar, and ends of the second signal sub-lines 62 away from the first signal sub-lines 61 are electrically connected with each other through a second short-circuiting bar; each first short-circuiting bar 7 is connected with one driving chip 3; each second short-circuiting bar 8 is connected to another driving chip 3.

In this case, as shown in FIG. 9, each of the first signal sub-line 61 and the second signal sub-line 62 of each bias signal line 6 is connected with one driving chip 3 through the first short-circuiting bar or the second short-circuiting bar. The driving chips 3 connected with the first short-circuiting bars are disposed on one side edge of the base substrate 1 along the second direction, and the driving chips 3 connected with second short-circuiting bars are disposed on the other side edge of the base substrate 1 along the second direction. The driving chips 3 on the same side edge of the base substrate 1 along the second direction are connected to the signal line groups, respectively, so that the driving chips 3 are arranged closely.

In this way, the number of the driving chips 3 required to be provided is increased. That is, in a case where the total number of the bias signal lines 6 is constant, since each bias signal line 6 includes the first signal sub-line 61 and the second signal sub-line 62, the number of signal line groups into which the bias signal lines 6 can be divided is increased, and the number of the driving chips 3 connected to the signal line groups is increased. Therefore, the driving load of each driving chip 3 is reduced, and when the bias signal in the signal line group is interfered by external interference, the bias signal of the signal line group can be quickly restored to normal, and the noise is reduced. Since an area of the detecting units 2 covered by the bias signal lines 6 connected with each driving chip 3 is reduced, the area controlled by each driving chip 3 is finer, which is beneficial to specific optimization adjustment of certain driving chips 3 or signal line groups, so that the grayscale image obtained after an output electric signal is processed is more uniform.

In some implementations, the bias signal line 6 and the data line 4 may be disposed on the same side of the detecting unit 2, may be disposed on two sides of the detecting unit 2, respectively, or may be disposed to run through the detecting unit 2. In a case where the bias signal line 6 and the data line 4 are disposed on the same side of the detecting unit 2, orthographic projections of the bias signal line 6 and the data line 4 on the base substrate 1 are at least partially overlapped, so that the aperture ratio of the detecting unit 2 can be increased, and the detection capability of the detecting unit 2 can be improved; in a case where the bias signal line 6 runs through the detecting unit 2, the orthographic projection of the bias signal line 6 on the base substrate 1 is at least partially overlapped with an orthographic projection of the photosensitive device 12 on the base substrate 1, so that a contact efficiency between the bias signal line 6 and the photosensitive device 12 can be improved, and the conduction efficiency of the detecting unit 2 can be improved; in a case where the bias signal line 6 and the data line 4 are disposed at both sides of the detecting unit 2, respectively, the wiring arrangement of the flat panel detector described above is facilitated.

FIG. 4 is an equivalent circuit diagram of the detecting unit 2. As shown in FIG. 4, in some implementations, the detecting unit 2 includes a switch sub-circuit 10 and a photosensitive device 12. The switch sub-circuit 10 includes a thin film transistor 11, the photosensitive device 12 includes a photodiode 13. A source of the thin film transistor 11 is connected to a data line 4, a drain of the thin film transistor 11 is connected to the photosensitive device 12, and a gate 14 of the thin film transistor 11 is connected to a scanning line 5. An anode of the photodiode 13 is connected to the thin film transistor 11, and a cathode of the photodiode 13 is connected to a bias signal line 6. An operation process of the detecting unit 2 is as follows: under an action of a bias voltage of the bias signal line 6, the photodiode converts a received optical signal into an electric signal, and inputs the electric signal to the drain of the thin film transistor 11; a control signal of the scanning line 5 is written into the gate 14 of the thin film transistor 11, the thin film transistor 11 is turned on, and the electric signal, converted by the photodiode 13, written into the drain of the thin film transistor 11, and then is written into the data line 4 via the source of the thin film transistor 11. In this way, the detection of the optical signal by the detecting unit 2 is completed.

In some implementations, the thin film transistor 11 may include an amorphous silicon thin film transistor or a metal oxide thin film transistor 11. In some implementations, the thin film transistor 11 in the embodiment of the present disclosure is the amorphous silicon thin film transistor, so that the structure of the detecting unit 2 is simple and easy to manufacture.

In some embodiments, the photodiode 13 includes a PIN photodiode. The PIN photodiode has the advantages of having mature preparation process and being easy to manufacture.

In some implementations, a photoelectric conversion layer is disposed on a side of the detecting unit 2 away from the base substrate 1; the photoelectric conversion layer is configured to convert an external electric signal into an optical signal. For example, the photoelectric conversion layer may be a scintillator layer, and in such implementations, a material constituting the scintillator layer is a material capable of converting X-rays into visible light, such as CsI: Tl and Gd2O2S:Tb, and CsI:Na, CaWO4, CdWO4, NaI:TI, BaFCI:Eu2+, BaSO4:Eu2+, BaFBr:Eu2+, LaOBr: Tb3+, LaOBr:Tm3+, La2O2S:Tb3+, YTaO4, YTaO4:Nb, ZnS:Ag, ZnSiO4:Mn2+, LiI:Eu2+, and CeF3 are also possible. The visible light obtained by converting the X-rays by a scintillation crystal contained in the scintillator layer may have a peak value of a wavelength in a range from 530 nm to 580 nm, and a spectral range from 350 nm to 700 nm. Such light has short delay effect, and can be attenuated to below 1% of irradiation brightness of the X-rays within 1 ms after the X-rays disappear.

In a second aspect, the present disclosure provides a detecting apparatus including the flat panel detector. In the embodiment of the present disclosure, the flat panel detector may be an X-ray flat panel detector, and the detecting apparatus includes, but is not limited to, an X-ray diagnostic imaging system (including a C-arm, DSA (digital subtraction angiography), DRF (digital radiography & floroscopy), oral CBCT (oral cone-beam computed tomography), and the like), a radiotherapy apparatus, an X-ray industrial nondestructive inspection detection, a safety inspection, a pet medical diagnosis, and the like.

It will be understood that the above embodiments are merely exemplary embodiments that are employed to illustrate the principles of the present disclosure, and that the present disclosure is not limited thereto. It will be apparent to those skilled in the art that various modifications and improvements can be made without departing from the spirit and scope of the present disclosure, and such modifications and improvements are also considered to be within the scope of the present disclosure.

What is claimed is:

1. A flat panel detector, comprising:

a base substrate, a plurality of driving chips, a plurality of scanning lines, a plurality of data lines, a plurality of bias signal lines, and a plurality of detecting units arranged in an array, the plurality of scanning lines, the plurality of data lines, the plurality of bias signal lines, and the plurality of detecting units are disposed on the base substrate; wherein each of the plurality of detecting units comprises a switch sub-circuit and a photosensitive device;

control terminals of switch sub-circuits in detecting units located in a same row are connected with a same scanning line;

first terminals of switch sub-circuits in detecting units located in a same column are connected with a same data line;

in each detecting unit, a second terminal of the switch sub-circuit is connected with a first terminal of the photosensitive device;

second terminals of photosensitive devices of the detecting units located in the same column are connected with a same bias signal line; and the plurality of bias signal lines is divided into a plurality of signal line groups, and bias signal lines in different signal line groups are insulated from each other and are connected with different driving chips.

2. The flat panel detector according to claim 1, further comprising a plurality of first short-circuiting bars and a plurality of second short-circuiting bars, wherein each of the plurality of bias signal lines comprises a first end and a second end that are oppositely disposed in a column direction;

in a same signal line group, first ends of bias signal lines are connected with each other by a first short-circuiting bar, and second ends of the bias signal lines are connected with each other by a second short-circuiting bar; and each first short-circuiting bar is connected with one of the plurality of driving chips, and/or each second short-circuiting bar is connected with one of the plurality of driving chips.

3. The flat panel detector according to claim 1, further comprising a plurality of first short-circuiting bars and a plurality of second short-circuiting bars, wherein each of the plurality of bias signal lines comprises a first end and a second end that are oppositely disposed in a column direction, first ends of bias signal lines of one of two adjacent signal line groups are connected with each other by a first short-circuiting bar, and second ends of bias signal lines of the other of the two adjacent signal line groups are connected with each other by a second short-circuiting bar, and each first short-circuiting bar is connected with one of the plurality of driving chips, and each second short-circuiting bar is connected with one of the plurality of driving chips.

4. The flat panel detector according to claim 1, further comprising a plurality of first short-circuiting bars and a plurality of second short-circuiting bars, wherein each of the plurality of bias signal lines comprises a first signal sub-line and a second signal sub-line arranged side by side in a column direction, and photosensitive devices connected to the first signal sub-line and the second signal sub-line are different;

for any signal line group, ends of first signal sub-lines away from second signal sub-lines are connected with each other by a first short-circuiting bar, and ends of the second signal sub-lines away from the first signal sub-lines are connected with each other by a second short-circuiting bar; and each first short-circuiting bar is connected with one of the plurality of driving chips, and each second short-circuiting bar is connected with one of the plurality of driving chips.

5. The flat panel detector according to claim 1, wherein the switch sub-circuit comprises a thin film transistor, a first electrode of the thin film transistor is connected with a corresponding data line of the plurlaity of data lines, a second electrode of the thin film transistor is connected with the photosensitive device, and a control electrode of the thin film transistor is connected with a corresponding scanning line of the plurality of scanning lines; the thin film transistor is configured to write an electric signal generated by the photosensitive device into the corresponding data line under a control of a control signal of the corresponding scanning line.

6. The flat panel detector according to claim 5, wherein the thin film transistor comprises an amorphous silicon thin film transistor or a metal oxide thin film transistor.

7. The flat panel detector according to claim 5, wherein the photosensitive device comprises a photodiode; a first electrode of the photodiode is connected with the thin film transistor, a second electrode of the photodiode is connected with a corresponding bias signal line of the plurality of bias signal lines; and the photodiode is configured to convert an optical signal received into an electric signal under a bias voltage of the corresponding bias signal line, and to input the electric signal to the second electrode of the thin film transistor.

8. The flat panel detector according to claim 7, wherein the photodiode comprises a PIN photodiode.

9. The flat panel detector according to claim 1, further comprising a photoelectric conversion layer on a side of the plurality of detecting units away from the base substrate, wherein the photoelectric conversion layer is configured to convert X-rays into visible light.

10. A detecting apparatus, comprising: the flat panel detector according to claim 1, and a display for displaying a detection result of the flat panel detector.

11. The detecting apparatus according to claim 10, wherein in each signal line group, bias signal lines extend from a detection area to a peripheral area, and end portions of the bias signal lines on a same side of the bias signal lines are connected together by a short-circuiting bar, which is bound and connected with a driving chip by a signal lead-out line.

12. The detecting apparatus according to claim 10, wherein the plurality of driving chips is arranged at a same end of the plurality of signal line groups along a column direction, and the plurality of driving chips are respectively connected to different ones of the plurality of signal line groups, and the plurality of signal line groups are insulated from each other.

13. The detecting apparatus according to claim 10, wherein driving chips connected to every two adjacent signal line groups are respectively located on two opposite sides of the base substrate along a column direction.

14. The detecting apparatus according to claim 10, wherein each of the plurality of bias signal lines comprises a first end and a second end that are oppositely disposed in a column direction, each of a first signal sub-line and a second signal sub-line of each of the plurality of bias signal lines is connected with a driving chip through a first short-circuiting bar or a second short-circuiting bar, driving chips connected with first short-circuiting bars are disposed on one side edge of the base substrate along a column direction, and driving chips connected with second short-circuiting bars are disposed on the other side edge of the base substrate along the column direction.

15. The detecting apparatus according to claim 10, wherein in a case where the plurality of bias signal lines and the plurality of data lines are disposed on a same side of the plurality of detecting units, orthographic projections of the plurality of bias signal lines and the plurality of data lines on the base substrate are at least partially overlapped.

* * * * *